(12) United States Patent
Richart

(10) Patent No.: US 11,109,953 B2
(45) Date of Patent: Sep. 7, 2021

(54) PACKAGE, PREFERABLY MEDICAL, AND CORRESPONDING SET OF PACKAGES

(71) Applicant: SELENIUM MEDICAL, La Rochelle (FR)

(72) Inventor: Olivier Richart, Le Bois Plage en Re (FR)

(73) Assignee: SELENIUM MEDICAL, La Rochelle (FR)

( * ) Notice: Subject to any disclaimer, the term of this patent is extended or adjusted under 35 U.S.C. 154(b) by 0 days.

(21) Appl. No.: 16/343,540

(22) PCT Filed: Oct. 17, 2017

(86) PCT No.: PCT/FR2017/052853
§ 371 (c)(1),
(2) Date: Apr. 19, 2019

(87) PCT Pub. No.: WO2018/078242
PCT Pub. Date: May 3, 2018

(65) Prior Publication Data
US 2019/0314133 A1 Oct. 17, 2019

(30) Foreign Application Priority Data
Oct. 25, 2016 (FR) ...................................... 1660342

(51) Int. Cl.
*A61F 2/00* (2006.01)
*A61B 50/30* (2016.01)
(Continued)

(52) U.S. Cl.
CPC ............ *A61F 2/0095* (2013.01); *A61B 50/30* (2016.02); *B29D 22/003* (2013.01);
(Continued)

(58) Field of Classification Search
CPC . A61F 2/0095; A61B 50/30; A61B 2050/006; A61B 2050/3006; B29D 22/003; B65D 77/0486
(Continued)

(56) References Cited

U.S. PATENT DOCUMENTS 5,823,342 A * 10/1998 Caudillo ................ A61F 2/0095
206/438
7,669,716 B2 * 3/2010 Lightner ............ B65D 77/0453
206/583
(Continued)

FOREIGN PATENT DOCUMENTS

FR 2656792 7/1991

OTHER PUBLICATIONS

International Search dated Jun. 20, 2017.

*Primary Examiner* — Jacob K Ackun
(74) *Attorney, Agent, or Firm* — Ipsilon USA, LLP

(57) ABSTRACT

The invention relates to a package (2; 3) for an object, preferably a medical object, the package comprising a bottom shell (21; 31); a top shell (22; 32) having a closure portion (24; 34) referred to as a "cap", and a connection portion (23; 33) in the form of a hollow body and connected to the closure portion (24) by a hinge (25) to enable the closure portion (24; 34) to tilt relative to the connection portion (23; 33) in order to release access to the inside of the bottom shell (21; 31) through the connection portion (23; 33). The connection portion (23; 33) is provided with a stiffener element (290; 390) and a sealing strip (4; 4') connects together the edges (241, 231) of the cap (24; 34) and of the connection portion (23; 33) that face each other over the entire length of said edges. Said connection portion
(Continued)

(23; 33) of the top shell (22; 32) and of the bottom shell (21; 31) are two parts that are fastened to each other, preferably by bonding.

10 Claims, 3 Drawing Sheets

(51) Int. Cl.
*B29D 22/00* (2006.01)
*B65D 77/04* (2006.01)
*A61B 50/00* (2016.01)
*A61F 2/32* (2006.01)

(52) U.S. Cl.
CPC .... *B65D 77/0486* (2013.01); *A61B 2050/006* (2016.02); *A61B 2050/3006* (2016.02); *A61F 2/32* (2013.01)

(58) Field of Classification Search
USPC .......................................................... 206/438
See application file for complete search history.

(56) References Cited

U.S. PATENT DOCUMENTS

| | | | |
|---|---|---|---|
| 2005/0016886 A1* | 1/2005 | Riley | A61L 2/26 |
| | | | 206/438 |
| 2010/0140124 A1 | 6/2010 | Hafner | |
| 2012/0048751 A1* | 3/2012 | Stopek | A61F 2/0095 |
| | | | 206/63.3 |
| 2014/0042050 A1* | 2/2014 | Richart | A61F 2/0095 |
| | | | 206/438 |
| 2016/0106507 A1 | 4/2016 | Richart | |

* cited by examiner

PACKAGE, PREFERABLY MEDICAL, AND CORRESPONDING SET OF PACKAGES

RELATED APPLICATION

This application is a National Phase of PCT/FR2017/052853 filed on Oct. 17, 2017, which claims the benefit of priority from French Patent Application Nos. 16 60342, filed on Oct. 25, 2016, the entirety of which are incorporated by reference.

FIELD OF THE INVENTION

The present invention relates in general manner to packages for objects, and in particular packages for preferably sterile medical parts.

PRIOR ART

Document FR 3 005 937 discloses a package and a double-package set of small size and in which each package is sealed by applying a sealing strip.

An object of the present invention is to propose a package and a double-package set in which the or each sealing strip can be applied in reliable manner on the opening zone of said package.

SUMMARY OF THE INVENTION

To this end, the invention provides a package for an object, preferably a medical object, said package comprising:
- a bottom shell; and
- a top shell;
the package being characterized in that the top shell comprises:
- a closure portion referred to as a cap; and
- a connection portion in the form of a hollow body, and connected to the cap by a hinge;
the connection portion being provided with a stiffener element spaced apart from the hinge; and
in that said package also comprises:
- a sealing strip connecting together the facing edges of the cap and of the connection portion over the entire length of said edges; and
- said connection portion of the top shell and the bottom shell being two parts that are fastened to each other, preferably by bonding.

Such a design for the package enables the sealing strip to be applied against the opening zone defined between the facing edges (or end peripheries) of the cap and of the connection portion, without any risk of deforming the opening zone defined by said edges, because of the stiffness imparted to the top shell by the stiffener element.

This produces a package, and as described in detail below, a double-package set, in which the or each sealing strip can be applied reliably to the opening zone of said package, with reduced risk of deforming the shell, thus making it possible to apply the strip correctly and thereby benefit from good sealing.

Thus, unlike the solution in the state of the art, there is no need to devise an opening zone of specific shape adapted to the use of a backing part in order to obtain good stiffness for the top shell and in order to be able to apply the sealing strip correctly.

By making the bottom shell and the top shell separately, in particular by making the connection portion of the top shell separately from the bottom shell, it is possible to devise a single model of top shell that is suitable for use with bottom shells of different shapes and/or lengths depending on the type of object that is to be contained in the package.

The operator can thus have a single part number for the top shell and a plurality of part numbers for bottom shells corresponding to a wide variety of shapes and/or lengths of objects to be housed in the package. After selecting the bottom shell of shape appropriate for the object, said object is inserted into the bottom shell and then its top end edge (or periphery) is bonded to the stiffener element of the top shell. The top shell is in the closed position in the sense that the cap is facing the connection portion.

According to an advantageous characteristic of the invention, the cap, the hinge, and the connection portion of the top shell are formed as a single piece by molding.

According to an advantageous characteristic of the invention, the stiffener element is also spaced apart from the perimeter of the opening of the top shell in order to enable the end portion of the top shell that extends between said stiffener element and the perimeter of the opening, to be inserted into the bottom shell.

According to an advantageous characteristic of the invention, the sealing strip is applied at one of its ends against the hinge, extends along the edges of the cap and of the connection portion, and returns to be applied against the hinge.

According to an advantageous characteristic of the invention, the connection portion of the top shell and the portion of the bottom shell that is to be bonded to said connection portion present a section of shape that is oblong or rectangular with rounded corners.

Preferably, said stiffener element is an outer collar.

The invention also provides a set comprising:
- a package as described above, referred to as the "inner" package, housing an object, such as a medical implant; and
- a package as described above, referred to as an "outer" package, in which the inner package is housed.

According to an advantageous characteristic of the invention, said set includes a protective cover for covering the top shell of the outer package, having the perimeter of its opening coming to bear against said stiffener element of the connection portion of the top shell.

The invention also provides a method of fabricating a set as described above, said method being characterized in that it comprises the following steps:
- molding the top shell as a single piece separately from the bottom shell, the cap of the top shell being in the closed position;
- unmolding the top shell;
- inserting an object in the bottom shell of the inner package;
- bonding the top shell of the inner package to the bottom shell of the inner package;
- before or after the bonding step, applying the sealing strip to the top shell of the inner package;
- inserting the inner package in the bottom shell of the outer package;
- bonding the top shell of the outer package to the bottom shell of the outer package; and
- before or after the bonding step, applying the sealing strip to the top shell of the outer package.

According to a particular aspect, the top shell of the outer package is bonded at said stiffener element, preferably a collar, to the free end periphery of the bottom shell of the outer package.

According to a particular aspect, the top shell of the inner package is bonded at said stiffener element, preferably a collar, to the free end periphery of the bottom shell of the inner package.

BRIEF DESCRIPTION OF THE DRAWINGS

Other characteristics and advantages of the invention appear further from the following description, which is purely illustrative and non-limiting and should be read with reference to the accompanying drawings, in which.

DETAILED DESCRIPTION

Figure 1:
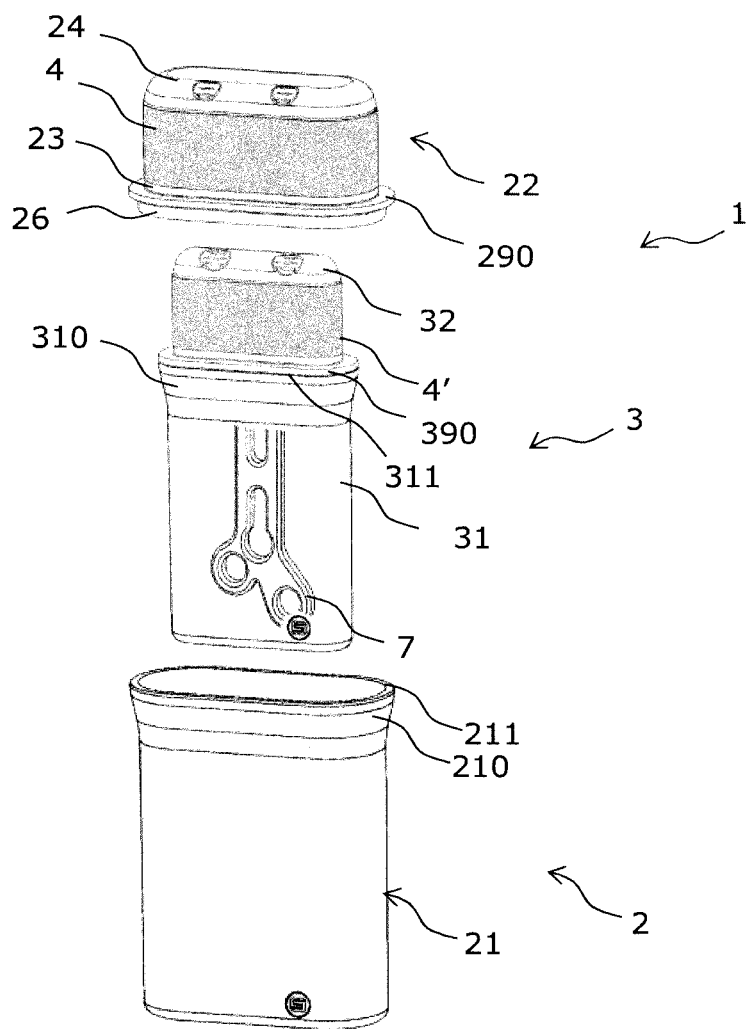
FIG. 1 is a perspective view of a set in accordance with an embodiment of the invention, shown with the inner package in the assembled state and prior to assembling together the top shell and the bottom shell of the outer package that house the inner package.

The concept of the invention is described more completely below with reference to the accompanying drawings, in which embodiments of the concept of the invention are shown. Similar numbers refer to elements that are similar in all of the drawings. Nevertheless, the concept of the invention can be embodied in numerous different forms and should not be interpreted as being limited to the embodiments described herein. On the contrary, these embodiments are proposed so that the description is complete and communicates the extent of the concept of the invention to persons skilled in the art. Consequently, the extent of the invention is defined by the accompanying claims. For reasons of simplification, the following embodiments are examined with reference to the terminology and the structure of a package and of a double package.

Throughout the specification, any reference to "an embodiment" means that a particular function, structure, or characteristic described with reference to an embodiment is included in at least one embodiment of the present invention. Thus, the term "in an embodiment" as used at various locations through the specification does not necessarily refer to the same embodiment. In addition, the particular functions, structures, and characteristics may be combined in any appropriate manner in one or more embodiments.

With reference to the figures, there is shown an assembly 1 comprising a first package 3, referred to as an inner package, containing a medical implant 7, and a second package 2, referred to as an outer package, in which the first package is housed. In a variant, provision may be made for the inner package 3 to contain an object other than a medical implant 7. The inner package 3 may contain one or more, preferably sterilized, medical parts that are other than the parts shown in FIGS. 1 and 2.

In particular, the assembly is designed for the purposes of preserving the sterile nature of said object and so as to enable the object to be unpacked under conditions that are aseptic or close to being aseptic. By way of example, said object may be a solid part, such as a screw for surgery, or any other type of object, in particular any other type of implant. In addition, said object could be a liquid or a powder. Said object, and preferably the various portions of the package, is/are sterilized, e.g. by radiation.

The inner package and the outer package have characteristics that are identical or similar, naturally with the exception of their dimensions.

Thus, the description below is applied to the outer package 2 that houses said inner package 3, but it also applies to the inner package 3 that contains the medical implant.

In the example shown in the figures, the outer package 2 comprises a bottom shell 21 and a top shell 22. The bottom shell 21 is in the form of a hollow body presenting a closed end wall and an opposite end that is open. Thus, each shell is considered as being an open shell in the sense that it forms a blind cavity and, when assembled with the other shell, serves to define a closed chamber once a sealing strip is in the applied state, as described in detail below. The open end portion 210 flares so as to receive a portion of the top shell.

The top shell 22 has a closure portion 24 referred to as a "cap", and a portion 23, referred to as a "connection portion", that is in the form of a hollow body. In particular, said connection portion is in the form of a segment of the top shell. The connection portion is generally cylindrical in shape, having its peripheral wall extending around the opening axis of said top shell.

The connection portion 23 is connected to the cap 24 by a hinge 25 so as to enable the cap 24 to be tilted relative to the connection portion 23 between a raised position (open) giving access to the inside of the connection portion, and a lowered position (closed) preventing access to the inside of said connection portion.

Once the top shell has been bonded to the bottom shell, the hinge between the cap and the connection portion of the top shell enables the cap to be opened so as to give access to the inside of the bottom portion 21 through the connection portion 23.

The hinge connects a fraction of the top periphery of the connection portion to the periphery of the cap. The bottom periphery of the connection portion is engaged in the flared top portion of the bottom shell 21.

The periphery of the cap has the same shape and the same size as the top periphery of the connection body. Thus, when the cap is in the closed position, said peripheries are situated facing each other and together they form said top shell, presenting one end that is closed and an opposite end that is open and communicates with the bottom shell.

The peripheral wall of the connection portion 23 is provided with a collar 290 that is preferably situated in the proximity of the bottom periphery of the top shell defining the opening in the top shell. In the example shown in the figures, said collar is an outer collar.

The collar 290 is spaced apart from the opening zone in the top shell as defined by the top periphery 231 of the connection portion and the corresponding periphery 241 of the cap so as to enable a sealing strip 4 to cover the opening zone as defined between said peripheries.

The collar 290 is for being pressed against the end periphery 211 of the opening of the bottom shell. The collar thus forms not only an element for stiffening the top shell, but also an abutment for limiting the extent to which the top shell engages in the bottom shell. The bottom shell and the top shell are for bonding together, preferably where the collar of the top shell is pressed against the free end periphery of the bottom shell. The face of the collar opposite from its face that is for pressing against the periphery of the free end of the bottom shell serves to receive the end periphery of the opening of the cover 9, as explained below.

In the example shown in the figures, the collar 290 is spaced apart from the bottom periphery of the top shell that defines the opening of the top shell so as to allow a portion of the peripheral wall, referred to as the "engagement portion" 26, of the top shell to be inserted in the bottom shell, and in particular in the flared portion of the bottom shell, as described below. The engagement portion of the top shell and the free end portion of the bottom shell are configured to enable said engagement portion of the top shell to be engaged in said free end portion of the bottom shell, the collar forming an abutment stop for such engagement.

Advantageously, the through section defined by the engagement portion (forming the opening of the top shell) is greater than the through section defined by the connection portion, but less than the area defined by the outer periphery of the collar.

As mentioned above, the sealing strip 4 on the outside of the top shell connects together the edges of the cap and of the connection portion that face each other when the cap is in its closed (or lowered) state, over the entire length of the edges of the shells of the package and from one side to the other so as to seal the package.

Figure 3:
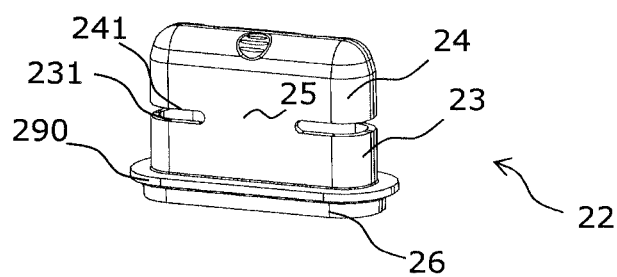
FIG. 3 is a perspective view of the top shell of the outer package, prior to applying the corresponding sealing strip, in accordance with an embodiment of the invention.
Figure 4:
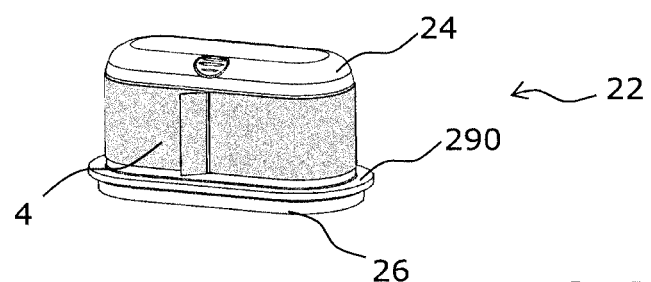
FIG. 4 is a perspective view of the top shell of the outer package, after applying the corresponding sealing strip, in accordance with an embodiment of the invention.
Figure 5:
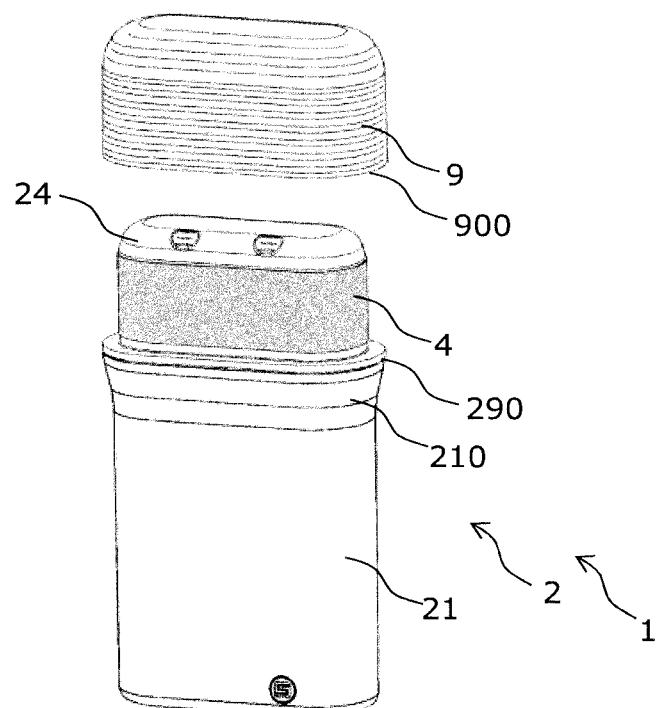
FIG. 5 is a perspective view of an assembly in accordance with an embodiment of the invention, said assembly including a protective cover for covering the top shell of the outer package.

The sealing strip 4 is preferably applied at one of its ends against the hinge 25, and then extends along the respective edges 241 and 231 of the cap 24 and of the connection portion 23, which edges extend facing each other, and returns to be applied against the hinge 25. As shown in FIG. 3, each of the edges 241, 231 terminates at the hinge 25 connecting the shells together.

This produces very good sealing against bacteria and liquid, without discontinuity along the opening zone of the top shell. Conversely, any overlap between one end of the strip and its other end over a fraction of the opening zone of the package would run the risk of poor sealing.

Preferably, the sealing strip 4 is a peel-off strip. Once the strip has been applied, it can be withdrawn by pulling on it to peel it off. The term "peel-off" is used to mean that the strip does not tear when it is removed, with adhesive remaining on the previously-sealed zones of the shells.

In a particular aspect, the sealing strip is applied to the package while hot and under pressure.

In an embodiment, said strip is a heat-sealing strip, e.g. made of non-woven synthetic material fabricated from polyethylene fibers, usually sold under the registered trademark TYVEK. It is possible to provide for replacing this solution for sealing while hot and under pressure with some other solution for sealing, e.g. using an appropriate chemical adhesive.

With a heat-sealing strip, the sealing strip 4 is applied to each of the packages 2 and 3 while hot and under pressure. The sealing strip 4 has one face provided with adhesive that becomes active when it is applied against the support that is to be sealed at given temperature and pressure.

In a variant, provision may be made for the strip to be tearable.

Once assembled together, said connection portion 23 of the top shell 22 and the bottom shell 21 form two parts that are fastened to each other in a manner that the user cannot take apart. Preferably, this fastening is performed by bonding between the collar and the free end periphery of the bottom shell.

In other words, the connection portion 23 of the top shell and the bottom shell 21 are not made as a single piece, but are made separately, and they are then fastened to each other in non-separable manner, i.e. so that a user cannot separate them from each other.

The cap 24 and the connection portion 23 of the top shell 22 are made as a single piece by molding. The shape of the mold is selected so that the cap is in its closed configuration (i.e. lowered), which is made possible by making the bottom shell separately, so that the top shell can be unmolded through its opening defined by the free end periphery that defines the opening of the top shell, while presenting a hinge 25 between the cap 24 and the connection portion 23. The connection portion 23 and the bottom shell 21 are then fastened together in inseparable manner, as described above.

In the example shown in the figures, the cap 24, the connection portion 23, and the hinge 25 connecting them together are formed as a single piece, preferably of plastics material.

The connection portion 23 of the top shell 22 and the free end edge 211 of the portion 210 of the bottom shell 21 that is to be bonded to said connection portion 23 present a section of shape that is oblong or rectangular with rounded corners in order to facilitate unmolding.

As explained above, the description made below for the package 2 applies equally to the package 3 that is received in the package 2 and that itself contains the medical implant 7. Thus, the above description may be read by replacing in the cited references the digit "2" by the digit "3" in order to obtain the references that correspond to the package 3. It should be observed that the sealing strip 4 described in the context of the package 2 corresponds for the package 3 to a sealing strip 4'.

Thus, the inner package 3 comprises a bottom shell 31 presenting an open end portion 310 and a free end periphery 311, and a top shell 32 comprising a cap 34, a connection portion 33 having a collar 390, a hinge (masked by the corresponding sealing strip 4' in FIGS. 1 and 2), and an engagement portion 36.

In an embodiment that is not shown in the figures, said set comprises an additional first package or inner package that is received in the outer package beside the other inner package. Advantageously, the packages are of section that is generally rectangular or square in general shape.

Said outer package 2 has a protective cover 9 enabling the top shell 21 of the outer package 2 to be covered with the periphery 900 of the opening in the cover coming to bear against the outer collar 290 of the connection portion 23 of the top shell 22.

Each package described above may be made using a fabrication method that comprises the following steps. The top shell 22 (or 32) is molded at a single piece separately from the bottom shell 21 (or 31). The shape of the mold corresponds to a configuration for the top shell in which the cap is in a said closed position, i.e. facing the connection portion.

The opening in the top shell defined by the free end periphery of the connection portion and situated at the end of the connection portion remote from the hinge enables the top shell to be unmolded easily, which would not be possible if the bottom shell and the top shell were made as a single piece.

Thus, the top shell can easily be obtained by molding and in a configuration in which the cap is in its lowered position facing the connection portion. So long as the bottom shell and the top shell of either package have not been bonded together, it is possible to insert the desired object into the corresponding package without needing to manipulate the hinge.

Likewise, after the inner package has been bonded, it is possible to insert the welded inner package into the as yet not bonded outer package, once more without any need to engage the hinge. Thereafter the bottom and top shells of the outer package are bonded together. For each package, the bonding corresponds to bonding the top shell at its outer collar to the free end periphery of the bottom shell. Because the hinge is not engaged while making each package and the corresponding set, it is possible to reduce any risk of either of the hinges being damaged, which hinges are made of plastics material integrally with the remainder of the top shell of the corresponding package.

In order to unpack the object, an operator needs to undo the sealing strip, open the outer package by tilting the cap by means of the plastics hinge, and then extract the inner package and repeat those operations in order to access the object contained in the inner package.

The hinge being made of plastics material enables the corresponding package to be made for single use, given that engaging the plastics hinge while opening the cap deforms it so that it can no longer return to its original closed position. In other words, opening the cap deforms the hinge plastically in such a manner that once it has been opened the cap can no longer be reclosed correctly, thereby serving to obtain a single-use package. In a variant, the hinge could be breakable.

In an embodiment, the bottom shells and/or the top shells are made of material that is translucent, preferably a material that is transparent.

In an embodiment, the opening zone of one or each package, as defined between the edges of the shells of said package, is closer to the end wall of one shell than to the end wall of the other shell of said package.

Figure 2:
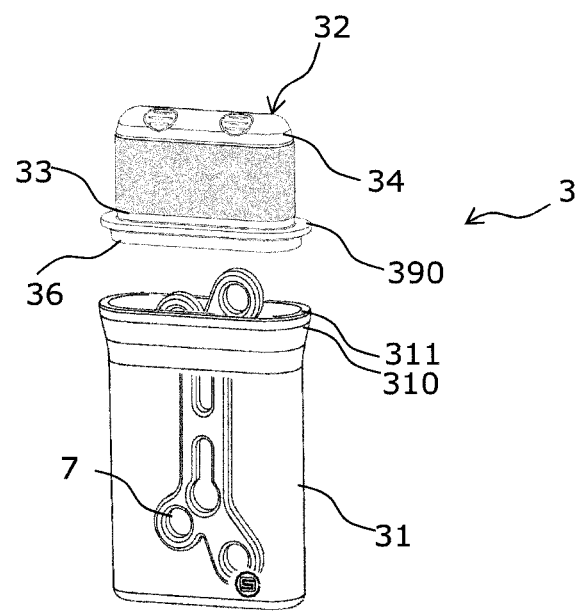
FIG. 2 is a perspective view of the inner package housing a medical implant, prior to assembling together the top shell and the bottom shell of said inner package, in accordance with an embodiment of the invention.
Figure 6:
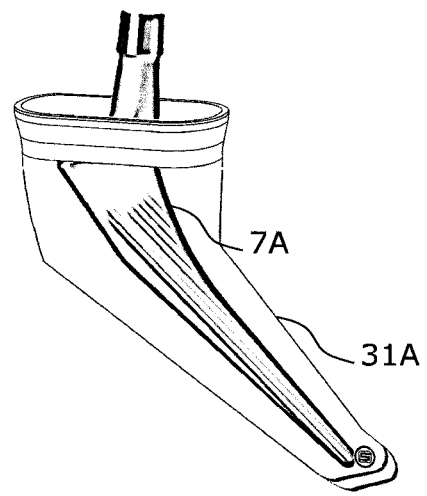
FIG. 6 is a perspective view of another model of the bottom shell of the inner package in accordance with an embodiment of the invention, the bottom shell having a shape that is suitable for housing a different object, such as a hip prosthesis.

As explained and as shown in FIG. 6, it is possible to fasten the top shell to a model of bottom shell that is different from the model shown in FIGS. 1 and 2. Thus, in the example shown in FIG. 6, the bottom shell 31A of the inner package is generally L-shaped and is adapted to receive a hip prosthesis 7A. Under such circumstances, the bottom shell of the outer package (not shown) is likewise generally L-shaped in order to be able to receive the bottom shell of the inner package.

The invention is not limited to the embodiments shown in the drawings. Consequently, it should be understood that when the characteristics mentioned in the accompanying claims are followed by reference signs, those signs are included solely for the purpose of improving the intelligibility of the claims and are not in any way limiting on the scope of the claims.

Furthermore, the term "comprising" does not exclude other elements or steps. In addition, characteristics and steps that are described with reference to one of the above-described embodiments may equally well be used in combination with other characteristics or steps of other embodiments described above.

The invention claimed is:

1. A package for an object said package comprising:
    a bottom shell; and
    a top shell;
    wherein the package the top shell comprises:
    a closure portion; and
    a connection portion configured in the form of a hollow body, and connected to the closure portion by a hinge;
    the connection portion being provided with a stiffener element configured to impart stiffness to the top shell, the stiffener element being spaced apart from the hinge; and
    in that said package also comprises:
    a sealing strip connecting together facing edges of the closure portion and of the connection portion over an entire length of said facing edges in such a manner as to seal the package; and
    the bottom shell and said connection portion of the top shell being two parts that are fastened to each other in a non-separable manner.

2. The package according to claim 1, wherein the closure portion, the hinge, and the connection portion of the top shell are formed as a single piece by molding.

3. The package according to claim 1, wherein said stiffener element is also spaced apart from the perimeter of the opening of the top shell in order to enable the end portion of the top shell that extends between said stiffener element and the perimeter of the opening, to be inserted into the bottom shell.

4. The package according to claim 1, wherein the sealing strip is applied at one of its ends against the hinge, extends along the edges of the closure portion and of the connection portion, and returns to be applied against the hinge.

5. The package according to claim 1, wherein the connection portion of the top shell and the portion of the bottom shell that is to be bonded to said connection portion present a section of shape that is oblong or rectangular with rounded corners.

6. The package according to claim 1, wherein said stiffener element is an outer collar.

7. A set comprising:
    two packages according to claim 1, a first of said two packages being an inner package, housing an object; and
    a second of said two packages being an outer package, having the inner package housed therein.

8. The set according to claim 7, wherein said set includes a protective cover for covering the top shell of the outer package, having the perimeter of its opening coming to bear against said stiffener element of the connection portion of the top shell.

9. The package according to claim 1, wherein the closure portion is a cap.

10. The package according to claim 1, wherein the bottom shell and said connection portion of the top shell are two parts that are fastened to each other by bonding.

* * * * *